United States Patent
Sawyer et al.

(10) Patent No.: US 9,801,731 B2
(45) Date of Patent: Oct. 31, 2017

(54) SPINAL IMPLANT AND METHODS OF MANUFACTURE THEREOF

(71) Applicant: University of Florida Research Foundation, Inc., Gainesville, FL (US)

(72) Inventors: Wallace Gregory Sawyer, Gainesville, FL (US); Brandon Alexander Krick, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 327 days.

(21) Appl. No.: 14/768,540

(22) PCT Filed: Jan. 31, 2014

(86) PCT No.: PCT/US2014/014119
§ 371 (c)(1),
(2) Date: Aug. 18, 2015

(87) PCT Pub. No.: WO2014/130224
PCT Pub. Date: Aug. 28, 2014

(65) Prior Publication Data
US 2016/0000575 A1 Jan. 7, 2016

Related U.S. Application Data

(60) Provisional application No. 61/766,566, filed on Feb. 19, 2013.

(51) Int. Cl.
*A61F 2/44* (2006.01)
*A61F 2/30* (2006.01)

(52) U.S. Cl.
CPC ............ *A61F 2/4425* (2013.01); *A61F 2/442* (2013.01); *A61F 2002/30224* (2013.01);
(Continued)

(58) Field of Classification Search
CPC .............................. A61F 2/442; A61F 2/4425
See application file for complete search history.

(56) References Cited

U.S. PATENT DOCUMENTS 6,136,031 A * 10/2000 Middleton .......... A61F 2/30744
623/17.16
6,579,321 B1 6/2003 Gordon
(Continued)

OTHER PUBLICATIONS

International Preliminary Report on Patentability for International Application No. PCT/US2014/014119; International Filing Date Jan. 31, 2014; Report dated Sep. 3, 2015 (8 pages).
(Continued)

*Primary Examiner* — Christian Sevilla
(74) *Attorney, Agent, or Firm* — Cantor Colburn LLP

(57) ABSTRACT

Disclosed herein is an intervertebral disc prosthesis comprising a first cantilever arm; the first cantilever arm comprising a shaft that is affixed to a disc; a second cantilever arm that comprises a plurality of rods that contact the disc; the plurality of rods being equidistant from a central axis of the shaft; and a third cantilever arm that comprises a platform to which are attached a plurality of rings; the rings being concentrically disposed about the shaft; the rings being in operative communication with each other; where the plurality of rods contacts the platform; and where the second cantilever arm has more degrees of freedom than the first cantilever arm, while the third cantilever arm has a number of degrees of freedom that are greater than or equal to the number of degrees of the second cantilever arm.

17 Claims, 6 Drawing Sheets

(52) U.S. Cl.
CPC .............. *A61F 2002/30235* (2013.01); *A61F 2002/30299* (2013.01); *A61F 2002/30563* (2013.01); *A61F 2002/30565* (2013.01); *A61F 2240/002* (2013.01)

(56) References Cited

U.S. PATENT DOCUMENTS

| | | | |
|---|---|---|---|
| 7,083,651 | B2 | 8/2006 | Diaz |
| 7,291,171 | B2 | 11/2007 | Ferree |
| 7,309,357 | B2 | 12/2007 | Kim |
| 7,331,994 | B2 * | 2/2008 | Gordon ................ A61F 2/442 623/17.13 |
| 7,563,286 | B2 | 7/2009 | Gerber |
| 7,819,920 | B2 | 10/2010 | Assaker |
| 7,892,285 | B2 | 2/2011 | Viker |
| 2006/0089714 | A1 | 4/2006 | Liu |
| 2007/0123990 | A1 | 5/2007 | Sharifi-Mehr |
| 2007/0233255 | A1 | 10/2007 | Song |
| 2008/0281423 | A1 * | 11/2008 | Sheffer .............. A61B 17/7062 623/17.11 |
| 2009/0164019 | A1 | 6/2009 | Hsu |
| 2009/0326656 | A1 | 12/2009 | De Villiers |
| 2010/0191287 | A1 * | 7/2010 | Bucci ................ A61B 17/7062 606/249 |
| 2011/0208307 | A1 | 8/2011 | Lechmann |

OTHER PUBLICATIONS

International Search Report for International Application No. PCT/US2014/014119; International Filing Date Jan. 31, 2014; Report dated May 1, 2014 (5 pages).

Written Opinion for International Application No. PCT/US2014/014119; International Filing Date Jan. 31, 2014; Report dated May 1, 2014 (6 pages).

* cited by examiner

Figure 1 (side view)

Figure 2 (top view)
(not to the same scale as the Figure 1)

Figure 3 (side view)

Figure 4 (isometric view of section AA' from Figure 2)

SPINAL IMPLANT AND METHODS OF MANUFACTURE THEREOF

CROSS-REFERENCE TO RELATED APPLICATIONS

This application is a US National Stage Application claiming priority to International Application No. PCT/US14/014119 filed on Jan. 31, 2014, which claims the benefit of U.S. Application No. 61/766,566, filed on Feb. 19, 2013, which is incorporated herein by reference in its entirety.

BACKGROUND

This disclosure relates to intervertebral spinal implants and to methods of manufacture thereof.

The human spine is a flexible structure comprised of thirty-three vertebrae. Intervertebral discs separate and cushion adjacent vertebrae in the spine. The intervertebral discs act as shock absorbers and allow bending between the vertebrae.

The human spine occasionally suffers damage (during accidents or from wear) and repairing this damage is often accomplished by implanting an intervertebral implant between two adjacent vertebrae to function as a disc prosthesis. Motion preservation intervertebral implants for use in spinal surgery are utilized to preserve motion at the motion segment that is impacted by the surgery. In general, currently available commercial motion preservation devices do not replicate the anatomical motions and reactions of an intervertebral disc. Specifically, certain implants restrict most motions at the impacted level to a limited amount of pivoting or pitching between the vertebrae. It is desirable to design and construct an intervertebral motion preservation implant that mimics physiological or anatomical motion of an intervertebral disc to repair a diseased or damaged disc to its original, anatomical dampening and motion limitations.

SUMMARY

Disclosed herein is an intervertebral disc prosthesis comprising a first cantilever arm; the first cantilever arm comprising a shaft that is affixed to a disc; a second cantilever arm that comprises a plurality of rods that contact the disc; the plurality of rods being equidistant from a central axis of the shaft; and a third cantilever arm that comprises a platform to which are attached a plurality of rings; the rings being concentrically disposed about the shaft; the rings being in operative communication with each other; where the plurality of rods contacts the platform; and where the second cantilever arm has more degrees of freedom than the first cantilever arm, while the third cantilever arm has a number of degrees of freedom that are greater than or equal to the number of degrees of the second cantilever arm.

Disclosed herein is a method of manufacturing an intervertebral disc prosthesis comprising manufacturing a shaft with a disc disposed at one end; the disc having a larger diameter than a diameter of the shaft; where the disc is concentric to the shaft; contacting the disc with a plurality or rods; where an axis of each rod of the plurality of rods is parallel to a central axis of the shaft; contacting a platform with each rod of the plurality of rods; where an end of the rods that contacts the platform is opposed to an end that contacts the disc; the platform being in contact with a ring; the ring being disposed on an outer periphery of the platform; and contacting the ring to a plurality of rings through a plurality of ribs; where each pair of ribs of the plurality of ribs contacts a pair of rings; and where each successive pair of ribs is displaced by 90 degrees from another pair of ribs in a neighboring pair of rings.

Disclosed herein is a method of using an intervertebral disc prosthesis comprising contacting a pair of opposing vertebra in a vertebral column with an intervertebral disc prosthesis that comprises a first cantilever arm; the first cantilever arm comprising a shaft that is affixed to a disc; a second cantilever arm that comprises a plurality of rods that contact the disc; the plurality of rods being equidistant from a central axis of the shaft; and a third cantilever arm that comprises a platform to which are attached a plurality of rings; the rings being concentrically disposed about the shaft; the rings being in operative communication with each other; where the plurality of rods contacts the platform; and where the second cantilever arm has more degrees of freedom than the first cantilever arm, while the third cantilever arm has a number of degrees of freedom that are greater than or equal to the number of degrees of the second cantilever arm; where an uppermost ring of the plurality of rings contacts a vertebra and where one end of the shaft contacts an opposing vertebra.

DETAILED DESCRIPTION

This invention relates to an intervertebral disc prosthesis that allows improved movement and range of motion for the recipient. The intervertebral disc prosthesis may be used as a replacement for vertebrae in a vertebral gap in the spine, with a lower portion of the intervertebral disc prosthesis contacting the highest vertebra just adjacent to the gap and an upper portion of the prosthesis contacting the lowest vertebra adjacent to the gap. The intervertebral disc prosthesis mimics the geometrical and mechanical characteristics of a normal human intervertebral disc or of a series of intervertebral discs. The intervertebral disc prosthesis can flex and pitch and can withstand torque in a manner similar to the intervertebral discs in a living being, especially human beings. For example, when acted on by any force or movement, the intervertebral disc prosthesis reacts similarly to the reaction of a normal human intervertebral disc. The intervertebral disc prosthesis may be used in any portion of the spine, but is preferably used as a replacement for cervical vertebrae that are located in the necks of living beings.

The intervertebral disc prosthesis disclosed herein comprises at least three cantilever arms—a first cantilever arm, a second cantilever arm and a third cantilever arm, each cantilever arm of which offers a greater number of degrees of freedom than the preceding cantilever arm. At least two of the cantilever arms disclosed herein contact existing vertebra in the vertebral column. For example, the second cantilever arm has more degrees of freedom than the first cantilever arm, while the third cantilever arm has more degrees of freedom than the second cantilever arm.

The first cantilever arm is a central shaft, one end of which is fixedly attached to a first vertebra. The second cantilever arm are a plurality of rods each of which have one end fixedly attached to the central shaft, while the third cantilever arm is a plurality of rings that are fixedly attached to the plurality of rods. At least one end of the plurality of rings contacts a second vertebra. It is to be noted that the first vertebra is opposedly disposed to the second vertebra.

Disclosed herein too is a method of manufacturing the intervertebral disc prosthesis. In one embodiment, the intervertebral disc prosthesis can be manufactured in a single monolithic piece (i.e., there are no pieces of be assembled together). The intervertebral disc prosthesis may also alternatively be manufactured in multiple pieces and then assembled together if desired. It can be advantageously manufactured by additive manufacturing (also known as 3D printing or rapid prototyping). In one embodiment, the intervertebral disc prosthesis can be molded in a single piece using compression or injection molding.

Figure 1:
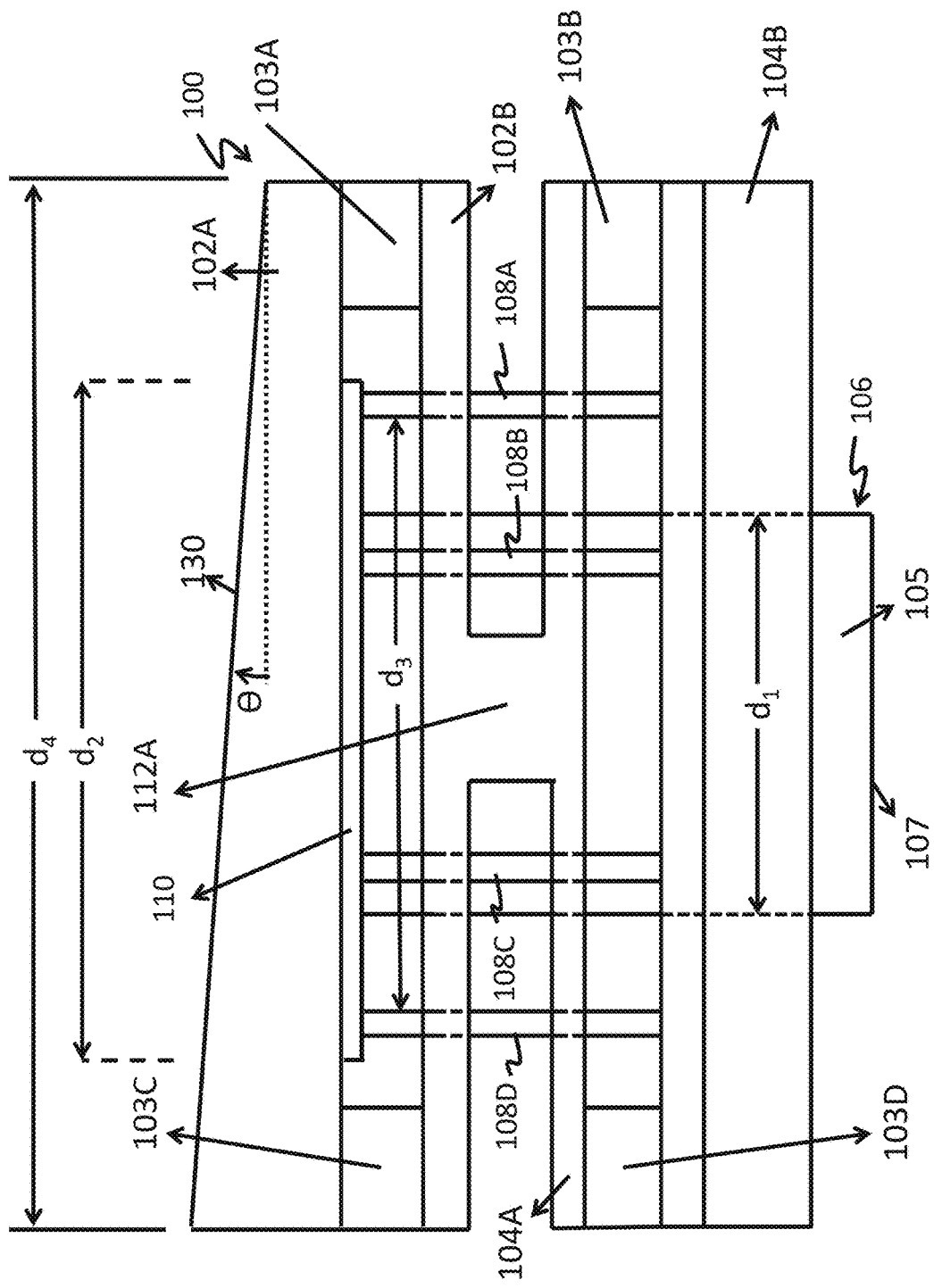
FIG. 1 is a side view of an exemplary intervertebral disc prosthesis.
Figure 2:
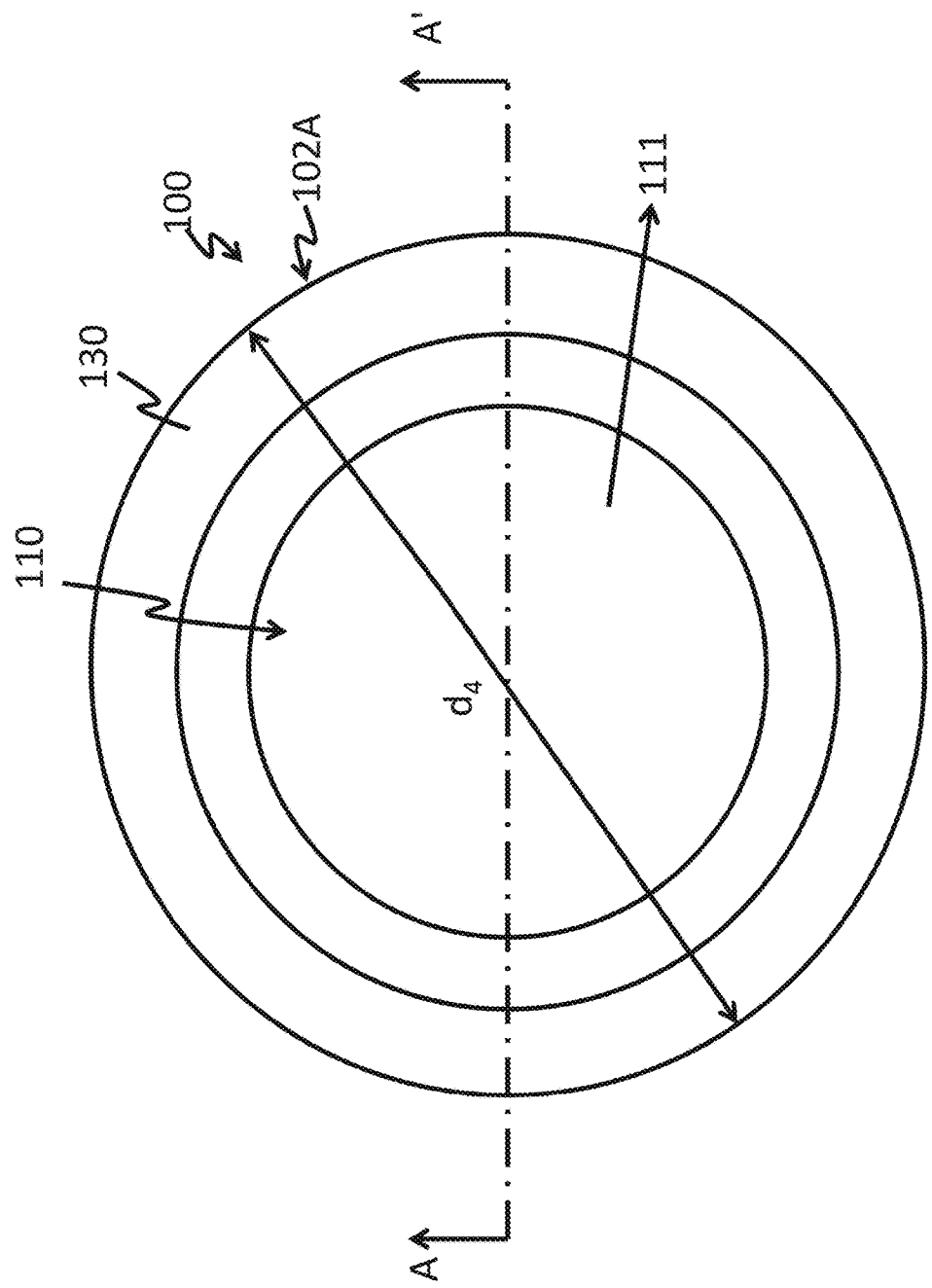
FIG. 2 represents a top view of the prosthesis of the FIG. 1, though not drawn to the same scale.
Figure 3:
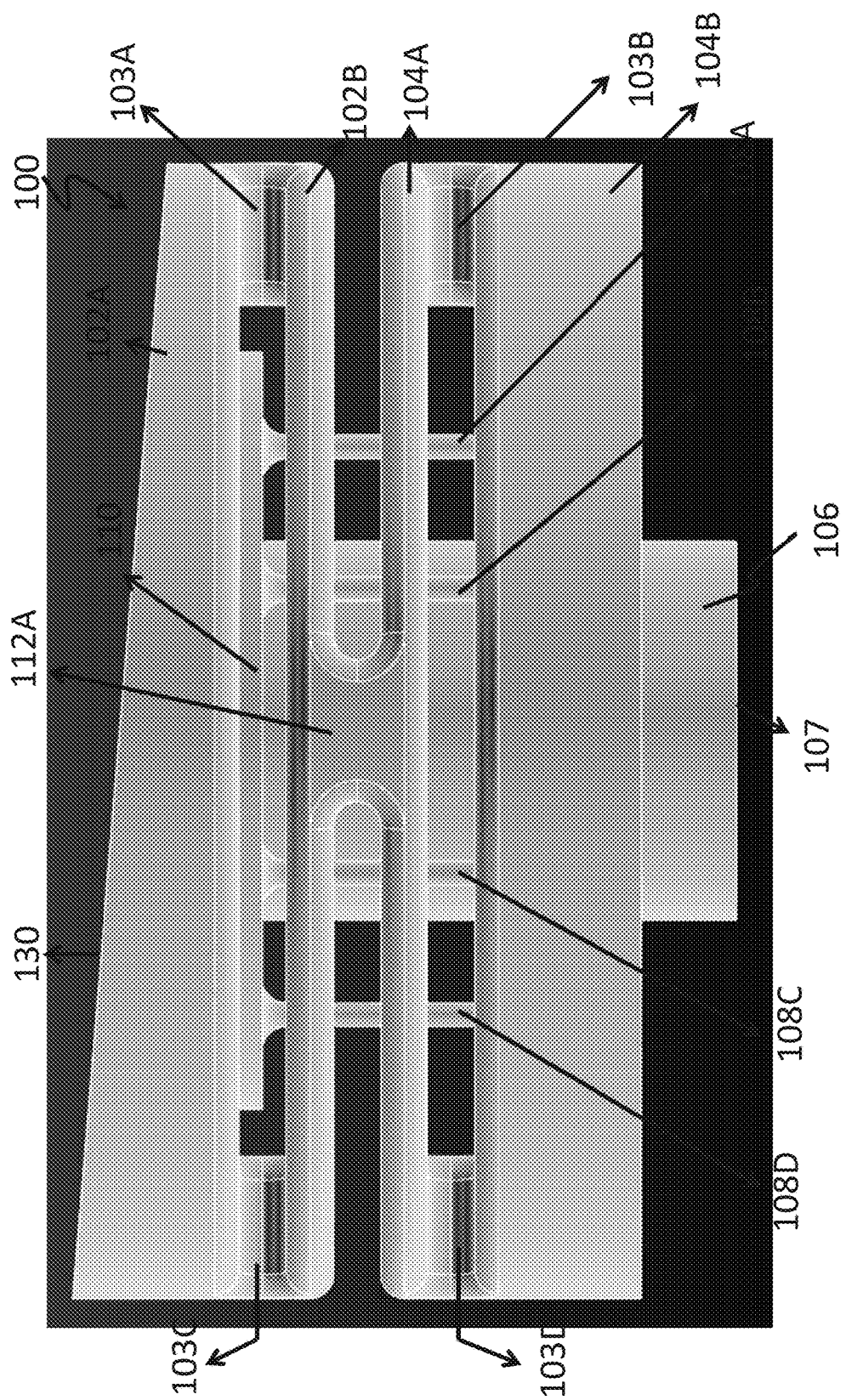
FIG. 3 is a computer illustration of the intervertebral disc prosthesis of the FIG. 1.
Figure 4:
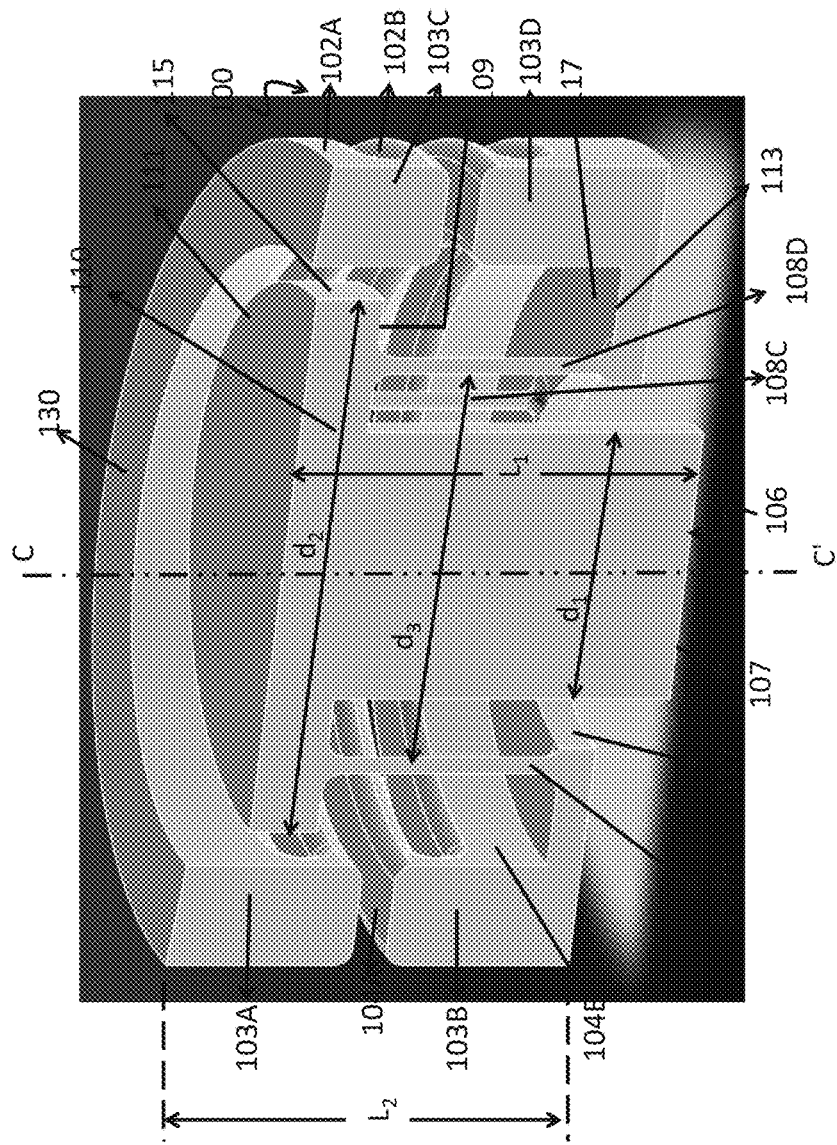
FIG. 4 is a computer illustration of an isometric view of the intervertebral disc prosthesis of the FIG. 1.

The FIG. 1 is a side view of an exemplary intervertebral disc prosthesis 100, while the FIG. 2 represents a top view of the same prosthesis. It is to be noted that the FIG. 2 is not drawn to the same scale as the FIG. 1. FIG. 3 is a computer illustration of an exemplary intervertebral disc prosthesis 100, while the FIG. 4 is a computer illustration of an isometric view of an exemplary intervertebral disc prosthesis 100.

With reference now to the FIGS. 1, 2, 3 and 4, an intervertebral disc prosthesis 100 comprises a central shaft 106 having a plate 112 disposed at one end. The plate 112 is in operative communication with a plurality of rods 108A, 108B, 108C and 108D that contact a plurality of rings 102A, 102B, 104A and 104B. An upper surface of the ring 102A and a lower surface of the central shaft 106 contacts the respective vertebra just adjacent to a gap in the vertebral column to permit the recipient to move a part of his/her body in a manner consistent with or identical to the manner in which he/she moved that particular part of his/her body prior to receiving the prosthesis.

The central shaft 106 comprises a cylinder 105 that has a first end 107 that contacts the vertebrae immediately adjacent to the gap in the vertebral column. The central shaft 106 functions as the first cantilever and contacts a vertebra at the first end 107 (not shown). While the first end 107 contacts the vertebra, the opposing end has a disc 110 that is free to pivot about the end 107. While the shaft 106 is described as having a circular cross-section in the FIGS. 1-4, the cross-section can be elliptical, square, triangular, rectangular, or the like. The end of the central shaft 106 opposite to the first end 107 has a disc 110 that is integral with the rest of the central shaft 106. The disc 110 has and upper surface 111 and a lower surface 109. The disc 110 is concentrically mounted on the central shaft 106 and has a larger diameter $d_2$ than the diameter $d_1$ of the central shaft (i.e., $d_2 > d_1$). The diameter $d_2$ is at least 1.3 to 5 times, specifically 1.5 to 4 times and more specifically 2 to 3 times the diameter of $d_1$.

Fixedly attached to the lower surface 109 of the disc 110 are a plurality of rods 108A, 108B, 108C and 108D that are in mechanical communication with a platform 113. The rods 108A, 108B, 108C and 108D function as cantilever arms (i.e., they form the second cantilever arm), which have a first end fixedly attached to the lower surface 109 of the disc 110. The opposite ends of the rods contact the platform 113, which is free to float about the point of attachment to the disc 110. The rods along with the platform 113 therefore pivot about their point of attachment to the disc 110. The second cantilever arm has a number of degrees of freedom that are greater than or equal to the degrees of freedom of the first cantilever arm. In an exemplary embodiment, the second cantilever arm has a greater number of degrees of freedom than the first cantilever arm.

The platform 113 is an integral part of the ring 104B which is in operative communication with the first ring 102. While the FIGS. 1 and 4 depict 4 rods (per half ring) that contact the disc 110 and the platform 113, it is possible to use 2 or more rods, 3 or more rods, 5 or more rods, 6 or more rods, and so on per half ring. In an exemplary embodiment, the intervertebral disc prosthesis 100 comprises 8 rods disposed between the disc 110 and the platform 113. The rods 108A, 108B, 108C, 108D, and so on, are in tension between the disc 110 and the platform 113, when the intervertebral disc prosthesis 100 is disposed in the vertebral column. While the rods are depicted as contacting the lower surface 109 of the disc 110, they may be fixedly attached to the outer curved surface 115 of the disc 110.

Figure 5:
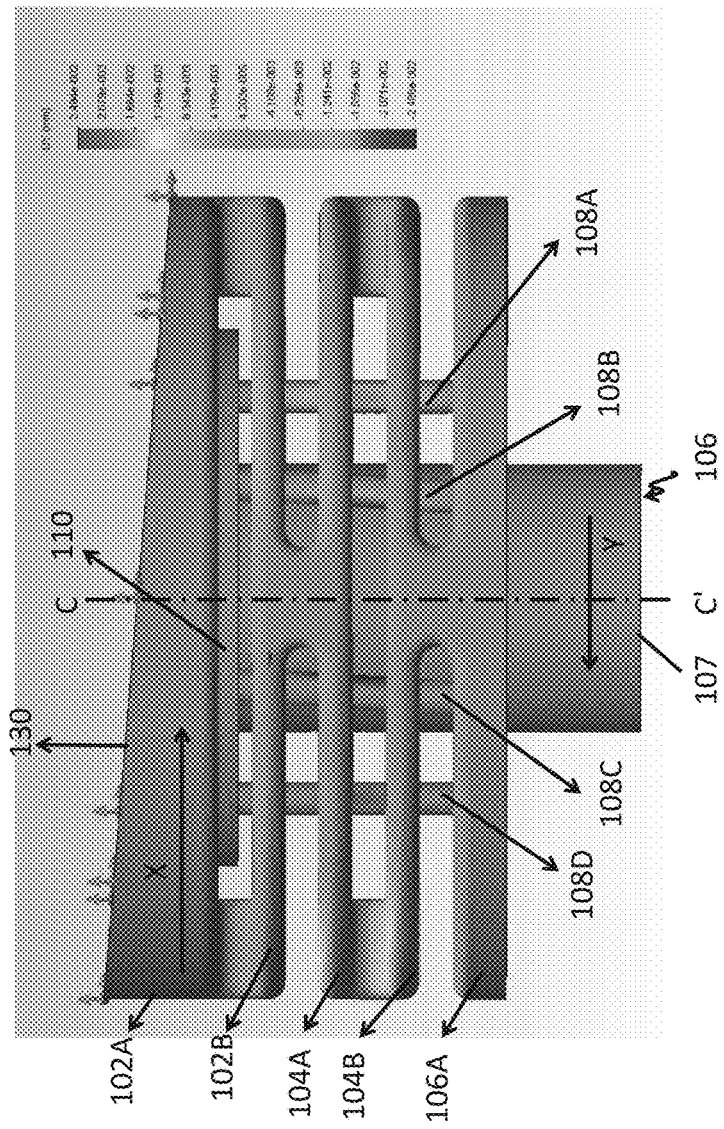
FIG. 5 is a depiction of an exemplary intervertebral disc prosthesis 100 that has 5 rings.

The rods 108 are manufactured from a material that renders them capable of bending, twisting and elongating when they are subjected to compression, torque and tension as part of the movement of the vertebral column and the movement of parts of the body that it supports. The FIG. 5 depicts an exemplary intervertebral disc prosthesis 100 when it is subjected to rotation. The parts have the same reference numerals as in the FIGS. 1-4. In the FIG. 5, it may be seen that when the intervertebral disc prosthesis 100 is rotated about its axis (i.e., when the ring 102 is rotated towards the right and the shaft 106 rotated to the left as indicated by the arrows X and Y respectfully), the rods 108A, 108B, 108C and 108D are subjected to forces that causes them to twist. It can be seen that the rod 108B, twists more than the other rods 108A, 108C and 108D.

If for example, the intervertebral disc prosthesis 100 is simultaneously subjected to bending and twisting, the rods 108A, 108B, 108C and 108D are subjected to compression and torque, while if the prosthesis 100 is simultaneously subjected to elongating and twisting, the rods 108A, 108B, 108C and 108D are subjected to tension and torque. In some embodiments, some of the rods may be subjected to only torque, while others may be subjected to either tension and compression in addition to torque. The rods always return to their original dimensions after being subjected to one or more of the aforementioned forces. The rods do not buckle.

The rods are generally cylindrical in shape and are equidistantly spaced from each other and equidistantly spaced from the axis C-C' of the intervertebral disc prosthesis 100. The rods are spaced along a circumference having a diameter $d_3$, where $d_3$ lies between $d_1$ and $d_2$. (See FIG. 4.) The rods are preferably flexible and manufactured from a material that returns to its original shape undergoing after deformation. While the figures in this disclosure depict rods, these may be substituted with springs or any other flexible geometrical configuration. It is desirable for the rods to be manufactured from a material that has an elastic modulus of 1 to 1,000 GPa. It can be manufactured from polymers or even harder materials such as diamond. In an exemplary embodiment, the rods comprise polymers. This is discussed in detail later.

The rods are molded in a single piece to the disc 110 and the platform 113. In an alternative embodiment, the rods may be adhesively bonded to the disc 110 and the platform 113. In yet another alternative embodiment, the rods may be screwed on or bolted to the disc 110 and the platform 113.

With reference now once again to the FIGS. 1, 2, 3 and 4, the platform 113 serves as the base of the lowermost ring 102 of the intervertebral disc prosthesis 100. The platform 113 is fixedly attached to the rods 108A, 108B, 108C and 108D. The rods may contact the upper surface 117 of the platform or alternatively contact the inner curved surface 119 of the platform 113. (See FIG. 4.) The rods 108 effectively serve as cantilever arms for the platform 113, while the platform 113 serves as a circular cantilever arm for the plurality of rings 102A, 102B, 104A, 104B, and so on.

The platform 113 supports a plurality of rings 102A, 102B, 104A, 104B, 106B, and so on. (See FIGS. 1, 3, 4 and 5.) The plurality of rings function as the third cantilever arm and pivot about their point of attachment to the platform 113. In one embodiment, the third cantilever arm has a number of degrees of freedom that is greater than or equal to about the number of degrees of freedom of the second cantilever arm. In an exemplary embodiment, the third cantilever arm has more degrees of freedom than the second cantilever arm. The upper surface of the uppermost ring has a taper (defined by an angle θ) that is designed to accommodate the vertebra that it contacts.

While the FIGS. 1, 3 and 4 depict four rings namely 102A, 102B, 104A, 104B, the number of rings that are cantilevered about the platform 113, the number of rings can be 2 or more, 3 or more, 5 or more, 6 or more, and so on. The number of rings is proportional to the number of missing vertebrae in the vertebral gap that the intervertebral disc prosthesis 100 is used to replace. The FIG. 5 is a depiction of an exemplary intervertebral disc prosthesis 100 that has 5 rings 102A, 102B, 104A, 104B and 106B. Each ring in the FIGS. 1, 3 and 4 is in contact with each of its neighboring rings at at least two or more points. The rings contact each other via ribs 103A, 103B, and so on that are integral with the respective rings. With reference now to the FIG. 3, it can be seen that the ring 104A contacts the ring 104B via ribs 103B and 103D, while ring 102B contacts the ring 104A via rib 112A and another rib (which is opposed to rib 112A) and is not shown). The ring 102A contacts the ring 102B via a pair of ribs 103A and 103C respectively. The ribs between a first pair of rings are offset by 90 degrees to the ribs between any neighboring pair of rings.

The rings are concentrically disposed with regards to the cylindrical shaft 106 and the disc 110. The rings have an outer diameter $d_4$ that is greater than $d_1$, $d_2$, and $d_3$. The rings surround the cylindrical shaft 106 and the disc 110 and form a protective shell for the ribs 108A, 108B, . . . and so on. When the rings are not deformed, they are all parallel to each other.

With reference to the FIG. 4, the length $L_1$ of the plurality of rings is greater than the $L_2$, the length of the cylindrical shaft 106. The ratio of $L_1$ to $L_2$ can range from 0.5 to 1 to 1:0.25, specifically 0.75:1 to 1:0.75, and more specifically 0.90:1 to 1:0.90.

As can be seen in the FIGS. 1, 3 and 4, the uppermost ring 102B has a tapered surface 130. The taper is used to provide the proper degree of contact with the vertebra to which the upper ring is fixedly attached. The taper has an angle θ, which can vary up to 5 degrees, specifically 1 to 4 degrees.

While the aforementioned description and figures show rings labeled 102A, 102B, and the like, these rings can also be substituted with springs or with other mechanical means that offer a similar amount of flexibility as the rings.

Figure 6:
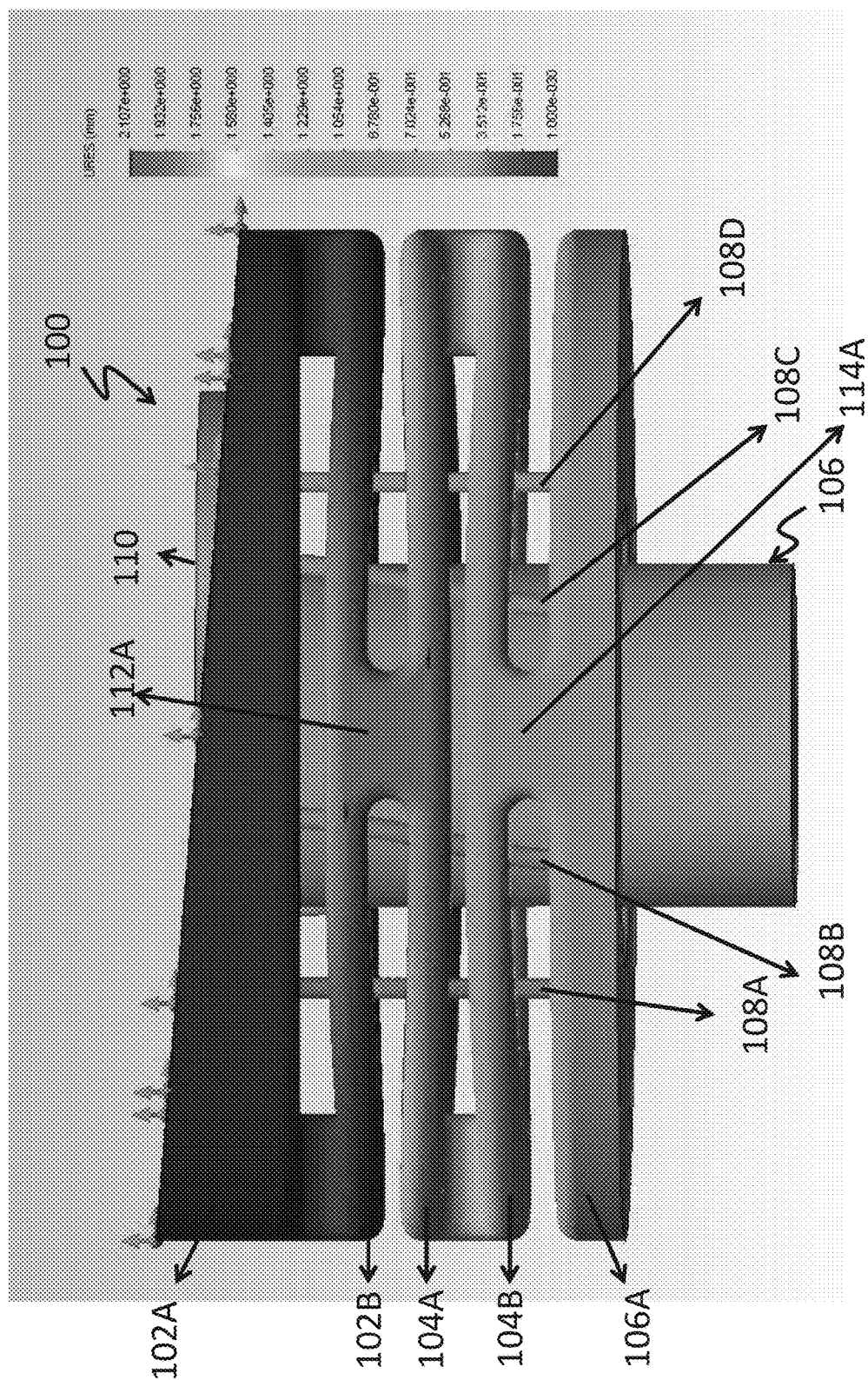
FIG. 6 depicts one embodiment of how the intervertebral disc prosthesis 100 functions when subjected to a compressive load with a sideways displacement (i.e., twisting).

The FIG. 6 shows one embodiment of how the intervertebral disc prosthesis 100 functions when subjected to a compressive load with a sideways displacement (i.e., twisting). From the FIG. 6, it may be seen that the respective rings undergo deformation due to the compressive force. The rings are deformed most at the regions between the ribs and deform the least near the ribs 112A and 114A. The portions of the rings near the ribs also come closer together as a result of the compressive deformation. The ribs 108A, 108B, 108C and 108D also undergo twisting and bending as a result of the torque applied to the intervertebral disc prosthesis 100.

The intervertebral disc prosthesis 100 can be manufactured from a wide variety of different materials. It is desirable for these materials to be compatible with fluids present in the body.

The intervertebral disc prosthesis 100 can be manufactured from materials that comprise metals, ceramics and polymers. When the intervertebral disc prosthesis 100 comprises metals and/or ceramics, it is desirable to use a coating of polymers over the metals and/or ceramics.

In an exemplary embodiment, it is desirable to manufacture the prosthesis from polymers. The polymers are organic polymers. Examples of suitable polymers are thermoplastic polymers, thermosetting polymers, blends of thermoplastic polymers, blends of thermosetting polymers, and blends of thermoplastic polymers with thermosetting polymers. The organic polymer can be a homopolymer, a copolymer, a block copolymer, an alternating copolymer, an alternating block copolymer, a random copolymer, a random block copolymer, a graft copolymer, a star block copolymer, an ionomer, a dendrimer, or a combination comprising at least one of the foregoing polymers. It is generally desirable to use polymers that have a glass transition temperature or a melting point that is higher than the temperature of the body of the recipient. If the glass transition temperature is lower than the recipient, then the polymer may be crosslinked to prevent the material from flowing after insertion.

The polymers are organic polymers and can be a polyacetal, a polyacrylic, a polycarbonate, a polystyrene, a polyester, a polyamide, a polyamideimide, a polyarylate, a polyarylsulfone, a polyethersulfone, a polyphenylene sulfide, a polyvinyl chloride, a polysulfone, a polyimide, a polyetherimide, a polytetrafluoroethylene, a polyketone, a polyetherketone, a polyether etherketone, a polyether ketone ketone, a polybenzoxazole, a polyoxadiazole, a polybenzothiazinophenothiazine, a polybenzothiazole, a polypyrazinoquinoxaline, a polypyromellitimide, a polyquinoxaline, a polybenzimidazole, a polyoxindole, a polyoxoisoindoline, a polydioxoisoindoline, a polytriazine, a polypyridazine, a polypiperazine, a polypyridine, a polypiperidine, a polytriazole, a polypyrazole, a polypyrrolidine, a polycarborane, a polyoxabicyclononane, a polydibenzofuran, a polyphthalide, a polyanhydride, a polyvinyl ether, a polyvinyl thioether, a polyvinyl alcohol, a polyvinyl ketone, a polyvinyl halide, a polyvinyl nitrile, a polyvinyl ester, a polysulfonate, a polynorbornene, a polysulfide, a polythioester, a polysulfonamide, a polyurea, a polyphosphazene, a polysilazane, a polyurethane, a polyfluorocarbon, a polysiloxane, or the like, or a combination including at least one of the foregoing polymers.

Exemplary polymers are aliphatic polyketones (e.g., polyketone (PK)), poly(ether ketones) (polyetherketone (PEK), polyetherketoneketone (PEKK), and polyetherketone etherketone ketone (PEKEKK)).

Another exemplary polymer is polysulfone. Exemplary polyarylsulfones that can be used include polyphenylsulfone that are available from sources such as Solvay Specialty Polymers, Quadrant EPP, Centroplast Centro, Duneon, GEHR Plastics, Westlake Plastics, and Gharda Chemicals. Commercial grades of polyphenylsulfones include those with the trade names Radel®, Udel®, Ultrason®, and Gafone®. An example of a polyarylsulfone includes those that are commercially available under the trade name Astrel® from 3M. Exemplary polyphenylene sulfides include those with either a branched structure, such as those marketed under the trade name Ryton® by Chevron-Phillips, a linear structure, such as those marketed under the trade name Fortron® by Ticona, or a combination thereof. Exemplary self-reinforced polyphenylenes that can be used include those that are commercially available under the trade name Primo Spire® PR-250 from Solvay Advanced Polymers. Exemplary polyethersulfones include those that are commercially available under the trade name Victrex PES® from ICI.

Exemplary thermoplastic polymers (crosslinked products) include crosslinked polyarylenes, crosslinked polyaryl sulfides, crosslinked polyaryl sulfones, and crosslinked polysulfones. In a particular embodiment, the crosslinked product is crosslinked polyphenylene sulfide (x-PPS), crosslinked polyphenylsulfone (x-PPSU), crosslinked self-reinforced polyphenylene (x-SRP), crosslinked polyethersulfone (x-PESU), or a combination comprising at least one of the foregoing.

In one embodiment, the intervertebral disc prosthesis 100 may be manufactured from a high glass transition temperature polymer such as polyetherketones or polysulfone and is coated with a biocompatible polymer such as polytetrafluoroethylene (commercially available as TEFLON®) or polydimethylsiloxane. Both the polytetrafluoroethylene and the polydimethylsiloxane may be crosslinked if desired.

The intervertebral disc prosthesis 100 can be manufactured by a number of different methods. In one embodiment, in one method of manufacturing the prosthesis, the various parts of the device can be manufactured separately and then assembled together. The various parts can be bonded together, screwed together and/or bolted together.

In another embodiment, the intervertebral disc prosthesis 100 can be manufactured in two halves, or 4 quarters and bonded together, screwed together and/or bolted together. In yet another embodiment, the device can be manufactured in a single integral monolithic piece. A monolithic piece is one that cannot be taken apart without dividing the device. The parts or the single piece can be manufactured by injection molding or by compression molding.

In another embodiment, the intervertebral disc prosthesis 100 can be manufactured by casting (e.g., investment casting). In yet another exemplary embodiment, the device can be manufactured in a single monolithic piece (i.e., a single indivisible unitary piece) by rapid prototyping.

In one method of using the intervertebral disc prosthesis 100, when a patient has a few cervical vertebrae removed they can be replaced by the prosthesis. The tapered surface 130 of the ring 102A contacts the lowest adjacent vertebra prior to the gap and the cylindrical shaft 106 contacts the highest adjacent vertebra prior to the gap. The tapered surface 130 is fixedly attached to the vertebra adjacent to the gap, while the cylindrical shaft 106 attached to the vertebra adjacent to the gap. The recipient will then be able to move in a manner similar to his/her movement prior to the damage to the spine.

The intervertebral disc prosthesis 100 is advantageous in that the design has a large number of degrees of freedom. The number of degrees of freedom of the prosthesis 100 is greater than or equal to 6, specifically greater than or equal to 8, specifically greater than or equal to 10, and more specifically greater than or equal to 12.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention.

What is claimed is:

1. An intervertebral disc prosthesis comprising:
   a first cantilever arm; the first cantilever arm comprising a shaft that is affixed to a disc;
   a second cantilever arm that comprises a plurality of rods that contact the disc; the plurality of rods being equidistant from a central axis of the shaft; and
   and a third cantilever arm that comprises a platform to which are attached a plurality of rings; the rings being concentrically disposed about the shaft; the rings being in operative communication with each other; where the plurality of rods contacts the platform; and where the second cantilever arm has more degrees of freedom than the first cantilever arm, while the third cantilever arm has a number of degrees of freedom that are greater than or equal to the number of degrees of the second cantilever arm.

2. The intervertebral disc prosthesis of claim 1, where an uppermost ring of the plurality of rings contacts a vertebra and where one end of the shaft contacts an opposing vertebra.

3. The intervertebral disc prosthesis of claim 2, where the plurality of rods comprises 4 or more rods.

4. The intervertebral disc prosthesis of claim 3, where the plurality of rods comprises 8 or more rods.

5. The intervertebral disc prosthesis of claim 4, where one end of each rod of the plurality of rods contacts the disc, while an opposing end of each rod of the plurality of rods contacts the platform.

6. The intervertebral disc prosthesis of claim 1, where the plurality of rings comprises 4 or more rings.

7. The intervertebral disc prosthesis of claim 6, where each ring of the plurality of rings contacts a neighboring ring through a pair of ribs.

8. The intervertebral disc prosthesis of claim 7, where the pair of ribs is displaced by 90 degrees from another pair of ribs in a neighboring pair of rings.

9. The intervertebral disc prosthesis of claim 8, comprising a metal or a ceramic.

10. The intervertebral disc prosthesis of claim 8, comprising an organic polymer.

11. The intervertebral disc prosthesis of claim 10, where the polymer is a polyetherketone.

12. The intervertebral disc prosthesis of claim 1, where the entire intervertebral disc prosthesis is a single unitary indivisible piece.

13. The intervertebral disc prosthesis of claim 1, where an upper surface of an uppermost ring of the plurality of rings has a tapered surface.

14. A method of manufacturing an intervertebral disc prosthesis comprising:
   manufacturing a shaft with a disc disposed at one end; the disc having a larger diameter than a diameter of the shaft; where the disc is concentric to the shaft;

contacting the disc with a plurality of rods; where an axis of each rod of the plurality of rods is parallel to a central axis of the shaft;

contacting a platform with each rod of the plurality of rods; where an end of the rods that contacts the platform is opposed to an end that contacts the disc; the platform being in contact with a ring; the ring being disposed on an outer periphery of the platform; and contacting the ring to a plurality of rings through a plurality of ribs; where a pair of ribs of the plurality of ribs contacts a pair of rings; and where a successive pair of ribs is displaced by 90 degrees from another pair of ribs in a neighboring pair of rings.

15. The method of claim 14, where the intervertebral disc prosthesis comprises a single monolithic piece.

16. The method of claim 14, where parts of the intervertebral disc prosthesis are bonded together, while other parts are mechanically fastened to each other.

17. A method of using an intervertebral disc prosthesis comprising:

contacting a pair of opposing vertebra in a vertebral column with an intervertebral disc prosthesis that comprises:

a first cantilever arm; the first cantilever arm comprising a shaft that is affixed to a disc;

a second cantilever arm that comprises a plurality of rods that contact the disc; the plurality of rods being equidistant from a central axis of the shaft; and a third cantilever arm that comprises a platform to which are attached a plurality of rings; the rings being concentrically disposed about the shaft; the rings being in operative communication with each other; where the plurality of rods contacts the platform; and where the second cantilever arm has more degrees of freedom than the first cantilever arm, while the third cantilever arm has a number of degrees of freedom that are greater than or equal to the number of degrees of the second cantilever arm; where an uppermost ring of the plurality of rings contacts a vertebra and where one end of the shaft contacts an opposing vertebra.

* * * * *